United States Patent [19]

Benazzi et al.

[11] Patent Number: 5,489,728
[45] Date of Patent: Feb. 6, 1996

[54] CATALYST FOR ALKYLATION OF $C_4$-$C_5$ ISOPARAFFIN BY AT LEAST ONE $C_3$-$C_6$ OLEFIN

[75] Inventors: Eric Benazzi, Montesson; Jean Francois Joly, Paris; Christian Marcilly, Houilles; Frederic Chaigne, Bauvoir S/Mer; Jean Yves Bernhard, Mennecy, all of France

[73] Assignee: Institut Francais du Petrole, Rueil Malmaison, France

[21] Appl. No.: 304,173

[22] Filed: Sep. 12, 1994

[30] Foreign Application Priority Data

Sep. 10, 1993 [FR] France .................................. 93 10896
Dec. 13, 1993 [FR] France .................................. 93 15047

[51] Int. Cl.[6] .................................................... C07C 2/62
[52] U.S. Cl. ........................ 585/731; 502/202; 502/216; 585/724; 585/730
[58] Field of Search .................... 585/730, 731, 585/726; 502/202, 216

[56] References Cited

U.S. PATENT DOCUMENTS 4,950,139 8/1990 Fennemann et al. .
5,233,119 8/1993 Kallenback et al. .

FOREIGN PATENT DOCUMENTS

| 2081271 | 4/1993 | Canada . |
| 67467 | 5/1982 | European Pat. Off. . |
| 325811 | 12/1988 | European Pat. Off. . |
| 433954 | 6/1991 | European Pat. Off. . |
| 539277 | 4/1993 | European Pat. Off. . |
| 2687935 | 9/1993 | France . |
| 2510095 | 9/1975 | Germany . |

*Primary Examiner*—Asok Pal
*Attorney, Agent, or Firm*—Millen, White, Zelano & Branigan

[57] ABSTRACT

The present invention relates to a catalyst comprising silica and an acid phase comprising sulphuric acid and the compound $HB(HSO_4)_4$, the silica having been impregnated by said acid phase, said catalyst being such that is consists essentially of particles of an average diameter of between 0.1 and 30 µm, prior to its impregnation with said acid phase, has a total porous volume of between 0.1 and 6 cm³ per gram and said acid phase contains between 0.4% and 68.8% by weight of the compound $HB(HSO_4)_4$, and between 31.2% and 99.6% by weight of the compound containing neither sulphuric anhydride nor boric acid.

The invention also relates to the preparation and use of said catalyst in catalytic alkylation of isobutane and/or isopentane in the presence of at least one olefin containing 3 to 6 carbon atoms per molecule.

14 Claims, No Drawings

CATALYST FOR ALKYLATION OF $C_4$–$C_5$ ISOPARAFFIN BY AT LEAST ONE $C_3$–$C_6$ OLEFIN

BACKGROUND OF THE INVENTION

The present invention relates to a catalyst comprising silica and an acid phase containing sulphuric acid and the compound $HB(HSO_4)_4$, the silica having been impregnated by said acid phase. The invention also relates to the preparation and use of said catalyst in catalytic alkylation of isoparaffin (isobutane and/or isopentane) in the presence of at least one olefin containing 3 to 6 carbon atoms per molecule.

In order to supply internal combustion engines which have spark ignition, and particularly engines with a high compression ratio, it is particularly advantageous to have fuels with high octane ratings, that is to say consisting essentially of heavily branched paraffin hydrocarbons. The alkylation of isoparaffins (isobutane and/or isopentane) by at least one olefin containing 3 to 6 carbon atoms per molecule allows such products to be obtained. This reaction requires the use of very acidic catalysts, particularly for reducing parasitic reactions such as hydride abstraction from the olefin and of polymerization which provide slightly branched hydrocarbons with a low octane rating and unsaturated hydrocarbons, cracking reactions and dismutation reactions.

The existing processes for production of hydrocarbons by alkylation of isobutane by olefins generally use either sulphuric acid or hydrofluoric acid as the catalyst. In these processes the acid catalyst constitutes a liquid phase which is placed in contact with the liquid isobutane/olefin(s) mixture to form an emulsion. These processes are expensive and give rise to significant problems with regard to personal and environmental safety. In order to remedy these problems, different catalytic systems of sulphuric acid and hydrofluoric acid in liquid phase have been sought.

In order to catalyze the alkylation reactions of isoparaffins by olefins, it has already been proposed to develop acid catalysts from numerous acid solids of different types. Amongst the families of acid catalysts, molecular sieves, macroreticular resins, possibly associated with $BF_3$, Lewis and/or Brönsted acids deposited on various inorganic supports, chlorous aluminiums, graphites interpenetrated with Lewis and/or Brönsted acids and anions deposited on oxide supports such as $ZrO_2/SO_4$ can be cited. These solids lead to the production of branched isoparaffins but suffer from several major faults, among which the use of often very high isobutane/olefin molar ratios to limit the magnitude of secondary reactions and the poor stability of the catalytic activity (inhibition of the catalyst by deposition of unsaturated oligomers) can be cited; these catalysts therefore have to be frequently regenerated. Moreover, the weak acidity of certain acid solids, such as molecular sieves, for example, necessitates the use of high reaction temperatures, which is prejudicial to obtaining hydrocarbons with a high octane rating.

European patent application EP-A-0539277 describes a catalyst containing silica and a solid acid phase comprising sulphuric acid; the silica according to said patent application is such that its porous volume is between 0.005 and 1.5 $cm^3$ per gram and its specific surface is between 0.01 and 1,500 $m^2$ per gram. Said acid phase can if required contain an additive selected from the group formed by $H_3PO_4$, $B(OH)_3$, $BF_4H$, $FSO_3H$, $CF_3CO_2H$, $SbF_5$, $CF_3SO_3H$ and $SO_3$.

French patent application FR-A-2 687 935 describes a catalyst containing a silica with a specific surface of between 0.01 and 1,500 $m^2$ per gram and a total porous volume of between 0.005 and 1.5 $cm^3$ per gram and an acid phase in solid state containing at least sulphuric acid and sulphuric anhydride, the silica having been impregnated with said acid phase. Said acid phase may possibly contain boric acid $B(OH)_3$, the content by weight of boric acid being between 0.01% and 50%.

SUMMARY OF THE INVENTION

The present invention relates to a catalyst comprising silica and an acid phase comprising sulphuric acid and the compound $HB(HSO_4)_4$, the silica having been impregnated with said acid phase, said catalyst being such that it is composed substantially of particles with an average diameter of between 0.1 and 30 μm (1 μm=$10^{-6}$m) and preferably between 5 and 30 μm such that the silica, before its impregnation with said acid phase, has a total porous volume of between 0.1 and 0.6 $cm^3$ per gram, preferably between 0.1 and 0.4 $cm^3$ per gram, and such that said acid phase contains (in % by weight) between 0.4 and 68.8%, preferably between 0.4 and 60% of the compound $HB(HSO_4)_4$ and between 31.2 and 99.6%, and preferably between 40 and 99.6% of the compound $H_2SO_4$, said acid phase being characterised by the fact that it contains neither sulphuric anhydride ($SO_3$) nor boric acid [$B(OH)_3$].

In particular, said acid phase does not contain non-associated sulphuric anhydride, that is to say not having reacted with the boric acid, nor non-associated boric acid, that is to say not having reacted with the sulphuric anhydride.

The content by weight of said catalyst in acid phase is generally between 1 and 40%, preferably between 1 and 30%.

The invention also relates to the preparation and use of said catalyst in catalytic alkylation of at least one isoparaffin selected from the group formed by isobutane and isopentane (that is to say isobutane and/or isopentane: isobutane, or isopentane, or isobutane and isopentane) in the presence of at least one olefin with 3 to 6 atoms of carbon per molecule.

The catalyst according to the present invention leads, in a surprising manner, to improved catalytic performance with respect to those described in European patent application EP-A-0539277 and also with respect to those described in French patent application FR-A-2 687 935.

The compound $HB(HSO_4)_4$ contained in the acid phase of the catalyst according to the invention can be obtained by all the methods known to the man skilled in the art. For example, and in a non-limiting manner, the preferred method according to the invention can be cited, which involves reacting 1 mol of boric acid $B(OH)_3$ with 3 mols of sulphuric anhydride $SO_3$ and 1 mol of sulphuric acid $H_2SO_4$ to obtain 1 mol of the compound $HB(HSO_4)_4$.

The silica as a support can contain impurities such as, for example, oxides, alkalines, alkaline-earths, aluminium compounds or any other impurities known to the man skilled in the art, the total quantity of the impurities generally not exceeding 2% by weight of the silica.

The silica is generally such that, before its impregnation with said acid phase, its specific surface is between 0.1 and 1,500 $m^2$ per gram. Moreover, said silica is generally constituted substantially of particles with an average diameter of between 0.1 and 30 μm, preferably between 5 and 30 μm.

The acid phase generally occupies between 80 and 100% of the total porous volume of the silica, preferably between 90 and 100% of said porous volume.

The process for preparation of the catalyst according to the invention generally comprises at least two stages. In a first stage the silica is calcined at a temperature greater than 50° C., preferably greater than 80° C. and even more preferably between 150° and 600° C., for example equal to approximately 500° C. The duration of this calcination stage is normally between 10 minutes and 50 hours, preferably between 15 minutes and 25 hours. The calcination is generally carried out in the presence of dry air or a dry air/nitrogen mixture, at a rate of between 0.001 and 10 liters per hour per gram, preferably between 0.1 and 5 l/h/g. The second stage consists of impregnation of said calcined silica with said acid phase. Any of the techniques well known to the man skilled in the art can be used to carry out this stage. A stage of preparation of the acid phase, prior to the impregnation stage can be added to this process of preparation.

The catalyst according to the invention thus prepared has not been subjected to any calcination subsequent to the impregnation stage. When it is used in the alkylation of isoparaffin(s) by at least one olefin, it is not subjected, prior to its use, to any calcination and thus between the impregnation stage and said use, it is not subjected to any calcination. The catalyst according to the invention thus prepared is therefore immediately ready for use.

The catalyst according to the present invention is used in a process which allows the alkylation reaction of isoparaffin by at least one olefin to be carried out in the best conditions. In particular said reaction being characterised by strong exothermic reaction (approximately 83.6 kJ per mol of transformed butene, if the olefin is butene and if the isoparaffin is isobutane), the use of the catalyst according to the present invention allows a good temperature homogeneity and concentration of reactants to be obtained.

In the process of alkylation of isoparaffin(s) using the catalyst according the present invention, the operating conditions, and more particularly the temperature and pressure, are generally selected in a manner such that the mixture constituted by the isoparaffin(s), the olefin(s) and the reaction products is liquid. Moreover, it is important that the catalyst is immersed in said liquid in order to ensure that there is a good liquid/solid contact.

The catalyst according to the invention is advantageously used in the reaction zone of alkylation of isobutane and/or isopentane with at least one olefin comprising 3 to 6 carbon atoms per molecule, in a liquid phase and in a mixture together with isoparaffin or a mixture of isoparaffins. The catalyst according to the invention can be used in an expanded bed, in an almost perfectly agitated reaction zone, or circulating bed, and is preferably used in a process which uses a continuous liquid phase, the catalyst being used in the form of a suspension, for example, according to the two implementations described hereinafter.

In the case where the catalyst is used in the form of a suspension, in a first implementation a reaction zone with an almost perfect mix can be used, that is to say with a perfect mix or near-perfect (agitated or Grignard vessel), using at least one agitation means, for example by means of a helix, in order to obtain sufficient agitation of the catalyst in suspension in the hydrocarbonated liquid phase, which consists generally of isoparaffin (isobutane and/or isopentane), at least one olefin, possibly at least one inert dilutant (for example, propane and normal butane) and the products of the alkylation reaction. The charge to be convened, composed of isobutane and/or isopentane and at least one olefin can be, for example, introduced in a liquid form at at least one point within the hydrocarbonated liquid phase present in the reaction zone.

A second implementation of the catalyst according to the present invention in suspension in a hydrocarbonated phase is the cocurrent flow fluidized bed or circulating bed. In this implementation the catalyst in suspension in the hydrocarbonated liquid phase, generally consisting of isoparaffin (isobutane and/or isopentane), at least one olefin, possibly at least one inert dilutant (for example propane or normal butane) and the products of the alkylation reaction, circulate from bottom to top in the reaction zone. The group constituted by the suspension of the catalyst in the hydrocarbonated phase then circulates through at least one heat exchanger and at least one pump, before being introduced again at the entrance to the reaction zone. The charge to be converted, constituted by isobutane and/or isopentane and at least one olefin is introduced either in liquid form or in gaseous form at at least one point in the reaction zone.

In the two types of implementation previously described, isoparaffin (isobutane and/or isopentane) not having been converted, or having been introduced in excess with respect to the stoichiometry of the reaction, is generally recycled after separation of the alkylate, either by direct introduction into the reaction zone or by mixing with the charge to be converted.

The isoparaffin(s)/olefin(s) mixture is generally introduced into the reaction zone at a spatial speed per hour, expressed in weight of olefin introduced per unit of catalyst and per hour (w.p.h.) of between 0.001 and $10h^{-1}$, and preferably between 0.002 and $2h^{-1}$. Said mixture can also be produced in the interior of the reaction zone. In all cases, the mixture constituted in this manner is in the reaction zone under conditions of pressure and temperature such that the mixture of hydrocarbons remains liquid on the catalyst.

The reaction temperature is generally lower than +10° C., preferably lower than 0° C. and in manner often more preferable, lower than −3° C. The pressure of the reaction zone is sufficient to maintain the hydrocarbons in a liquid state in said zone.

In order to limit secondary reactions, an excess of isoparaffin(s) with respect to the olefin(s) can be used. By way of example, in the case of alkylation of isobutane by a butene, the isobutane can be introduced pure in the charge or in the form of a mixture of butanes containing, for example, at least 40% isobutane. Moreover, a pure butane or else a mixture of isomeric butanes can be introduced. In any case, the isobutane/butene(s) molar ratio in the charge is generally between 1 and 100, preferably between 3 and 50 and in a manner often preferred, between 5 and 15.

When the nature of the catalyst and the reaction conditions and chosen judiciously (in particular the temperature), the catalyst according to the invention allows the production of alkylation products of at least one isoparaffin by at least one olefin which are valuable as fuels for engines and constituents for petrol, and which consist of, for example, at least 60% mols of paraffin having 8 atoms of carbon per molecule and less than 1% mols of non-saturated compounds, the paraffins consisting of 8 atoms of carbon per molecule composed of 70 to 98% in mols of trimethylpentanes.

Another advantage of the catalyst according to the present invention is the possibility of alkylizing isoparaffin with mixtures of olefins with 3 to 6 carbon atoms per molecule at low temperatures, where the proportion of olefins with 4 atoms of carbon per molecule is very significant.

The following examples illustrate the invention without thereby limiting the scope thereof.

EXAMPLE

Example 1

Preparation of catalyst 1 according to the invention 30 g of silica with a porous volume equal to 0.15 cm$^3$ per gram, with particles of an average diameter equal to 18 Nm and with a specific surface equal to 210 m$^2$ per gram is activated by drying in air at 150° C. for 12 hours. The silica thus activated is preserved in nitrogen. After this 2.97 g of boric acid is added to 100 g of sulphuric anhydride in sulphuric acid, containing 11.5% by weight of sulphuric anhydride and 88.5% by weight of sulphuric acid to obtain 102.97 g of acid phase.

After the reaction of the sulphuric anhydride and the boric acid in the presence of sulphuric acid, and respectively in molar ratios 3/1/1, an acid phase is obtained which contains the compound $HB(HSO_4)_4$ in solution in $H_2SO_4$ and containing 18.6% by weight of $HB(HSO_4)_4$ and 81.4% by weight of $H_2SO_4$.

After this dry impregnation of 20 g of said calcined solid with 5.15 g of the mixture described above is carried out. The solid thus obtained, designated catalyst 1, has a content by weight of acid phase equal to 20.5%. It is kept protected from humidity and in argon at −18° C.

Alkylation of isobutane by butene-1 with catalyst 1

20 g of catalyst 1 prepared according to the method described above 1 is introduced into a glass reactor of the Fischer & Porter type with a volume of 360 ml, previously purged by argon discharge. The reactor containing the catalyst is then closed, then placed under low vacuum, then cooled to the temperature of −20° C.

157 cm$^3$ of isobutane is then added to the reactor containing the catalyst while agitating, said reactor being immersed in a cold bath at −20° C. The catalyst +isobutane system is kept agitated for 30 minutes in order to homogenize the temperature.

2 g of butene-1 is added hourly regularly for a total of 6 hours, the temperature of the reactor being maintained at −8.5° C. for the whole duration of the injection.

After reaction, the hydrocarbon phase is drawn off from the reactor, then the isobutane is slowly evaporated and the alkylate is collected and analyzed by chromatography in the vapour phase. Its composition by weight is given in table 1. The olefin conversion is 100%.

Example 2

Preparation of catalyst 2 (not according) to the invention

To prepare catalyst 2, 20 g of the same silica as used for the preparation of catalyst 1 is used, the calcination conditions being identical. The solid thus activated is preserved in argon. 20 g of said calcined silica is then dry impregnated with 5.15 g of a solution of acid containing 86% by weight of sulphuric acid with a titre of 99.7% by weight, and 14% by weight in trifluoromethane sulphonic acid with a titre equal to 98% by weight. The solid obtained has a content by weight of acid phase equal to 20.5%. It is kept protected from humidity and in argon at −18° C.

Alkylation of isobutane by butene-1 with catalyst 2

The test of catalytic alkylation of isobutane by butene-1 in repeated under the same experimental conditions as those described in example 1. The results are described in table 1.

Example 3

Preparation of catalyst 3, not according to the invention

To prepare catalyst 3, 20 g of the same silica as used for the preparation of catalysts 1 and 2 is used, the calcination conditions being identical. The solid thus activated is preserved in argon. 20 g of said calcined silica is then dry impregnated with 5.15 g of sulphuric acid with a titre of 100% by weight. The solid obtained has a content by weight of acid phase equal to 20.5%. It is kept protected from humidity and in argon at −18° C.

Alkylation of isobutane by butene-1 with catalyst 3

The test of catalytic alkylation of isobutane by butene-1 is repeated under the same experimental conditions as those described in examples 1 and 2. The results are described in table 1.

TABLE 1

| Alkylate composition (% by weight) | Catalyst 1 (according to the invention) | Catalyst 2 (not according to the invention) | Catalyst 3 (not according to the invention) |
| --- | --- | --- | --- |
| $C_5$–$C_7$ % | 5.9 | 10.2 | 12.1 |
| $C_8$ % | 86.2 | 78.5 | 71.8 |
| $C_9^+$ % | 7.9 | 11.3 | 16.1 |

This table shows the advantage of working with a catalyst according to the invention, containing an acid phase composed of sulphuric acid and the compound $HB(HSO_4)_4$.

We claim:

1. A catalyst containing silica and an acid phase comprising sulphuric acid and $HB(HSO_4)_4$, the silica having been impregnated with said acid phase and said catalyst being such that it consists essentially of particles with an average diameter of 0.1 to 150 μm, such that the silica, prior to its impregnation with said acid phase, has a total porous volume of 0.1 to 0.6 cm$^3$ per gram, said acid phase containing (in % by weight) 0.4% 0.4% to 68.8% of $HB(HSO_4)_4$ and 31.2% to 99.6% of $H_2SO_4$, and said acid phase not containing sulphuric anhydride or boric acid.

2. A catalyst according to claim 1 consisting essentially of particles of average diameter of 5 to 30 μm.

3. A catalyst according to claim 1, wherein the content by weight of acid phase of said catalyst is 1 to 40%.

4. A process for the preparation of the catalyst according to claim 1, comprising calcining the silica at a temperature greater than 50° C. for a duration of 10 minutes to 50 hours, and impregnating said calcined silica by said acid phase.

5. A process according to claim 4 in which the compound $HB(HSO_4)_4$ is obtained by reacting 1 mol of boric acid with 3 mols of sulphuric anhydride and 1 mol of sulphuric acid.

6. A process for catalytic alkylation of at least one isoparaffin selected from the group consisting of isobutane and isopentane with at least one olefin containing 3 to 6 carbon atoms per molecule, said process comprising subjecting said isoparaffin and olefin to alkylation conditions in the presence of a catalyst of claim 1, in which process the reaction temperature is lower than +10° C. and the pressure of the reaction zone is sufficient to maintain the hydrocarbons in liquid state in said zone.

7. A process according to claim 6 in which the catalyst is used in a near-perfect mix reaction zone.

8. A process according to claim 6 in which the catalyst is used in a cocurrent flow fluidized bed.

9. A catalyst according to claim 1, wherein the total process volume of the silica prior to impregnation is 0.1 to 0.4 cm$^3$/g.

10. A catalyst according to claim 1, wherein the acid phase contains 0.4 to 60% by weight HB(SO$_4$)$_4$.

11. A catalyst according to claim 1, wherein the acid phase contains 40 to 99.6% by weight H$_2$SO$_4$.

12. A catalyst according to claim 1, wherein the content by weight of acid phase of said catalyst is 1 to 30%.

13. A catalyst according to claim 1, wherein the acid phase occupies 80–100% by weight of the total porous volume of the silica.

14. A catalyst according to claim 1, wherein the acid phase occupies 90–100% by weight of the total porous volume of the silica.

* * * * *